(12) United States Patent
Parakulam et al.

(10) Patent No.: US 8,535,821 B2
(45) Date of Patent: Sep. 17, 2013

(54) OPTICAL LEAK DETECTION SENSOR

(71) Applicant: Deeya Energy, Inc., Fremont, CA (US)

(72) Inventors: Gopalakrishnan R. Parakulam, Cupertino, CA (US); Saroj Kumar Sahu, Mountain House, CA (US); Rick Winter, Orinda, CA (US)

(73) Assignee: Deeya Energy, Inc., Fremont, CA (US)

( * ) Notice: Subject to any disclaimer, the term of this patent is extended or adjusted under 35 U.S.C. 154(b) by 0 days.

(21) Appl. No.: 13/735,835

(22) Filed: Jan. 7, 2013

(65) Prior Publication Data

US 2013/0188190 A1 Jul. 25, 2013

Related U.S. Application Data

(62) Division of application No. 12/790,749, filed on May 28, 2010, now Pat. No. 8,349,477.

(60) Provisional application No. 61/182,077, filed on May 28, 2009.

(51) Int. Cl.
*H01M 10/48* (2006.01)
*G01B 11/00* (2006.01)
*G01N 7/00* (2006.01)

(52) U.S. Cl.
USPC ............. 429/90; 429/91; 356/400; 356/927; 73/31.05; 73/61.48; 257/433

(58) Field of Classification Search
USPC ........... 429/90, 91, 61, 63, 50; 320/DIG. 13; 356/400, 927, 130, 4.07; 73/31.05, 40, 61.48; 257/82, 84, 98, 99, 433, E33.001
See application file for complete search history.

(56) References Cited

U.S. PATENT DOCUMENTS

| | | | |
|---|---|---|---|
| 6,337,559 B1 * | 1/2002 | Sato | 320/134 |
| 2007/0241758 A1 * | 10/2007 | Kamata | 324/537 |
| 2008/0137807 A1 * | 6/2008 | Yukisada et al. | 378/45 |

* cited by examiner

*Primary Examiner* — Raymond Alejandro
(74) *Attorney, Agent, or Firm* — Haynes and Boone LLP

(57) ABSTRACT

A leak detection sensor for detecting a leakage of an electrolyte solution in a flow battery system is provided. The sensor includes a sensor housing, the sensor housing being at least partially surrounded by a fluid and having mounted therein at least one light source. The device also includes at least one light detector, wherein light emitted from at least one light source is incident on a portion of the housing in contact with a fluid and is at least partially refracted by an amount which is dependent on a refractive index of the refractor lens and the surrounding fluid, such that the amount of refraction at the refractor lens and the surrounding fluid causes a loss in a power of light detected by the at least one light detector, the light detector determines the intensity of the detected light, determines the composition of fluid surrounding the device housing based on the based on the difference between the measured light intensity and the intensity of light produced by the light source, and determines a leak if the composition of fluid is determined to be an electrolyte solution.

2 Claims, 7 Drawing Sheets

OPTICAL LEAK DETECTION SENSOR

REFERENCE TO RELATED APPLICATIONS

This application is a divisional of U.S. patent application Ser. No. 12/790,749, filed on May 28, 2010, which claims the benefit of U.S. Provisional Application No. 61/182,077 filed on May 28, 2009. The contents of these applications are herein incorporated by reference in their entirety.

BACKGROUND OF THE INVENTION

1. Field of the Invention

Embodiments disclosed herein may be directed to a sensor for detecting a fluid leak, specifically an optical sensor which detects a leak based on transmittance properties of the fluid. In particular, embodiments disclosed herein may be directed to an optical leak detection sensor for detecting a leak in a flow cell battery system.

2. Description of the Relevant Art

Reduction-oxidation (redox) flow batteries store electrical energy in a chemical form, and subsequently dispense the stored energy in an electrical form via a spontaneous reverse redox reaction. A redox flow battery is an electrochemical storage device in which an electrolyte containing one or more dissolved electro-active species flows through a reactor cell where chemical energy is converted to electrical energy. Conversely, the discharged electrolyte can be flowed through a reactor cell such that electrical energy is converted to chemical energy. Electrolyte solution is stored externally, for example in tanks, and flowed through a set of cells where the electrochemical reaction takes place. The electrolyte tanks and cells may often be stored in a housing, which offers protection for the electrolyte tanks and cells. Externally stored electrolytes can be flowed through the battery system by pumping, gravity feed, or by any other method of moving fluid through the system. The reaction in a flow battery is reversible. The electrolyte, then, can be recharged without replacing the electroactive material. The energy capacity of a redox flow battery, therefore, is related to the total electrolyte volume, e.g., the size of the storage tank. However, the electrolytes in the system and stored in the tank may be corrosive to the housing and other components of the battery, and possibly even harmful to people and the environment, if leaked to the exterior of the housing. Accordingly, it is important to monitor the components of the flow battery system for electrolyte leakage.

Many leakage sensors used in batteries and other environments to detect a leak of a hazardous or corrosive fluid, will detect the presence of a fluid and then provide an indication that there is a leak. However, in many instances, the fluid being detected is not indicative of a leak. Rather, the fluid may be ambient or environmental fluid, such as rain water. When a leakage sensor indicates a leak due to a fluid such as rain water, it takes time for a person to investigate the so-called leak, and determine that there is not, in fact, a leak. Accordingly, it is important to not only monitor the components of a flow battery system for electrolyte leakage, but also to discern between electrolyte solution and other fluids.

SUMMARY OF THE INVENTION

In one embodiment, a redox flow cell battery system includes a pair of electrodes disposed in separate half-cell compartments; a porous or ion-selective membrane separating the half-cell compartments; and an electrolyte that is flowed through the half-cell compartments, wherein the electrolyte is stored in one or more electrolyte storage containers. A leak detector is positioned external to one or more of the electrolyte storage containers. The leak detector includes a device housing, the device housing having bottom surfaces. The leak detector also includes at least one light source in the device housing, the at least one light source emitting light that at least partially reflects from the bottom surfaces of the device housing, and is at least partially refracted by the bottom surfaces and fluid in contact with at least a portion of the bottom surface that the light is incident upon; and at least one light detector in the device housing, the light detector receiving the partially reflected light.

In accordance with some embodiments, there is provided a leak detection sensor for detecting a leakage of an electrolyte solution in a flow battery system. The sensor includes a sensor housing, the sensor housing being coupled to control electronics and is at least partially surrounded by a fluid and including a shielding member and a refractor lens, and having mounted therein at least one light source. The device also includes at least one light detector, wherein light emitted from the at least one light source is incident on the refractor lens and is at least partially refracted by an amount which is dependent on a refractive index of the refractor lens and the refractive index of the surrounding fluid, such that the amount of refraction at the refractor lens and the surrounding fluid causes a loss in a power of light detected by the at least one light detector, the light detector determines the power of the detected light, the control electronics converts the determined power into a corresponding frequency, the control electronics determine the type of fluid surrounding the device housing based on the frequency; and determines a leak if the type of fluid is determined to be an electrolyte solution.

Control electronics are used to control operation of the flow cell battery system, and are coupled to the leak detector. The control electronics determine the composition of fluid in contact with at least a portion of the bottom surfaces of the leak detector based on the difference between the measured light intensity and the intensity of light produced by the light source. If the determined composition of the fluid indicates the presence of the electrolyte solution, the control electronics shuts down the redox flow cell battery system.

In an embodiment, a method of detecting a fluid leak in a redox flow cell battery system, the redox flow cell battery system comprising a pair of electrodes disposed in separate half-cell compartments; a porous or ion-selective membrane separating the half-cell compartments; and an electrolyte that is flowed through the half-cell compartments, wherein the electrolyte is stored in one or more electrolyte storage containers, and a leak detector is positioned external to one or more of the electrolyte storage containers. The leak detector includes a device housing, the device housing including bottom surfaces; at least one light source in the device housing; and at least one light detector in the device housing. During use, light is emitted from the light detector. The emitted light is at least partially reflected from the bottom surfaces of the device housing, and is at least partially refracted by the bottom surfaces and fluid in contact with at least a portion of the bottom surface that the light is incident upon. At least a portion of the at least partially reflected and partially refracted light is detected using at least one of the light detectors. The composition of fluid in contact with at least a portion of the bottom surfaces of the leak detector is determined based on the difference between the measured light intensity and the intensity of light produced by the light source.

In another embodiment, a leak detector includes a device housing, the device housing comprising bottom surfaces; at least one light source in the device housing, the at least one light source emitting light that at least partially reflects from the bottom surfaces of the device housing, and is at least partially refracted by the bottom surfaces and fluid in contact with at least a portion of the bottom surface that the light is incident upon; and at least one light detector in the device housing, the light detector receiving the partially reflected light; and control electronics coupled to the leak detector. The control electronics determine type of fluid in contact with at least a portion of the bottom surfaces of the leak detector based on the difference between the measured light intensity and the intensity of light produced by the light source.

BRIEF DESCRIPTION OF THE DRAWINGS

Advantages of the present invention will become apparent to those skilled in the art with the benefit of the following detailed description of embodiments and upon reference to the accompanying drawings in which.

Figure 1:
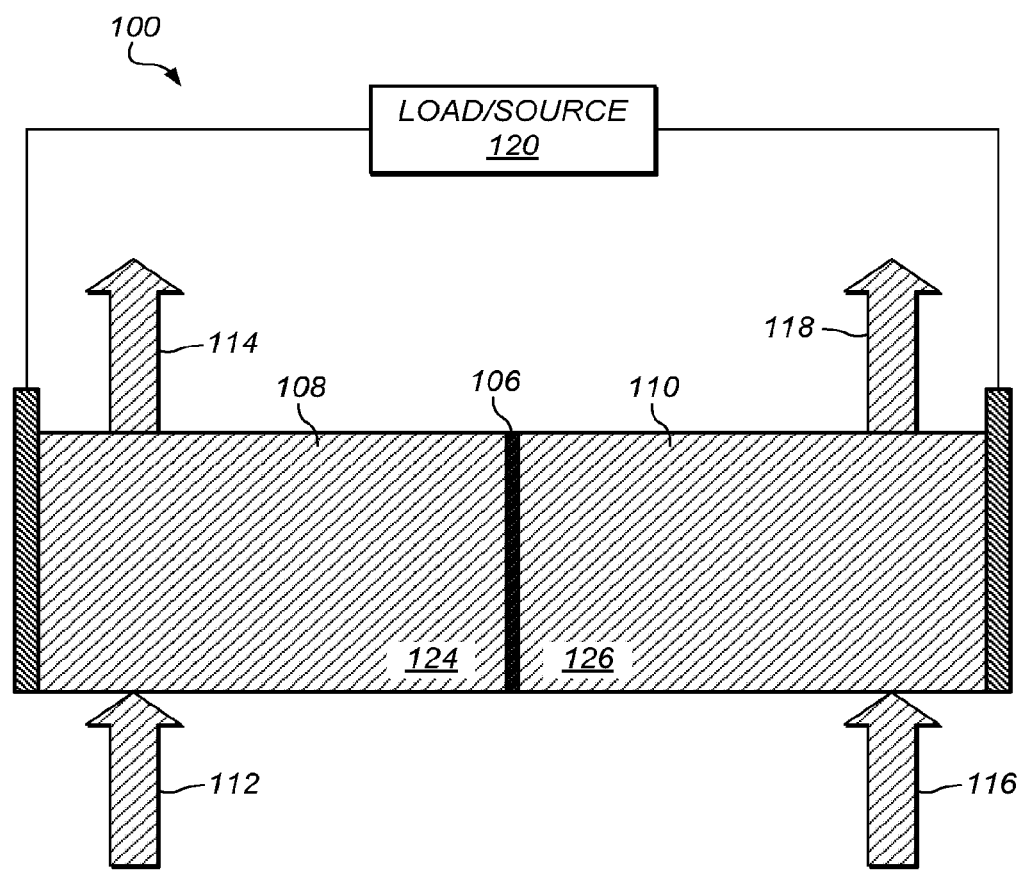
FIG. 1 depicts a flow battery system.

While the invention may be susceptible to various modifications and alternative forms, specific embodiments thereof are shown by way of example in the drawings and will herein be described in detail. The drawings may not be to scale. It should be understood, however, that the drawings and detailed description thereto are not intended to limit the invention to the particular form disclosed, but to the contrary, the intention is to cover all modifications, equivalents, and alternatives falling within the spirit and scope of the present invention as defined by the appended claims.

DETAILED DESCRIPTION OF THE PREFERRED EMBODIMENTS

It is to be understood the present invention is not limited to particular devices or methods, which may, of course, vary. It is also to be understood that the terminology used herein is for the purpose of describing particular embodiments only, and is not intended to be limiting. As used in this specification and the appended claims, the singular forms "a", "an", and "the" include singular and plural referents unless the content clearly dictates otherwise.

Reference will now be made in detail to embodiments disclosed in the accompanying drawings. Wherever possible, the same reference numbers will be used throughout the drawings to refer to the same or like parts.

FIG. 1 illustrates a flow battery system 100 according to some of the embodiments described herein. As shown, flow battery system 100 includes two half-cells 108 and 110 separated by a membrane 106. An electrolyte 124 is flowed through half-cell 108 and an electrolyte 126 is flowed through half-cell 110. Half-cells 108 and 110 include electrodes 102 and 104 respectively, in contact with electrolytes 124 and 126, respectively, such that redox reactions occur at the surface of the electrodes 102 or 104. In some embodiments, multiple flow battery systems 100 may be electrically coupled (e.g., stacked) either in series to achieve higher voltage or in parallel in order to achieve higher current. As shown in FIG. 1, electrodes 102 and 104 are coupled across load/source 120, through which electrolytes 124 and 126 are either charged or discharged. The operation of a flow cell and the composition of a membrane is further described in U.S. patent application Ser. No. 12/217,059, entitled "Redox Flow Cell," filed on Jul. 1, 2008, which is incorporated herein by reference. Construction of a flow cell stack is described in U.S. patent application Ser. No. 12/577,134, entitled "Common Module Stack Component Design" filed on Oct. 9, 2009, which is incorporated herein by reference.

When filled with electrolyte, one half-cell (e.g., 108 or 110) of flow battery system 100 contains anolyte 126 and the other half-cell contains catholyte 124, the anolyte and catholyte being collectively referred to as electrolytes. Reactant electrolytes may be stored in separate tanks and dispensed into the cells 108 and 110 via conduits coupled to cell inlet/outlet (I/O) ports 112, 114 and 116, 118 respectively, often using an external pumping system. Therefore, electrolyte 124 flows into half-cell 108 through inlet port 112 and out through outlet port 114 while electrolyte 126 flows into half-cell 110 through inlet port 116 and out of half-cell 110 through outlet port 118.

At least one electrode 102 and 104 in each half-cell 108 and 110 provides a surface on which the redox reaction takes place and from which charge is transferred. Suitable materials for preparing electrodes 102 and 104 generally include those known to persons of ordinary skill in the art. Examples of electrodes 102 and 104 are also described in U.S. patent application Ser. No. 12/576,235, entitled "Magnetic Current Collector" filed on Oct. 8, 2009, which is incorporated herein by reference. Flow battery system 100 operates by changing the oxidation state of its constituents during charging or discharging. The two half-cells 108 and 110 are connected in series by the conductive electrolytes, one for anodic reaction and the other for cathodic reaction. In operation (i.e., charge or discharge), electrolytes 126 and 124 (i.e., anolyte or catholyte) are flowed through half-cells 108 and 110 through I/O ports 112, 114 and 116, 118 respectively as the redox reaction takes place. Power is provided to a load 120 or received from power source 120, depending on if the flow cell battery is in discharging or charging mode, respectively.

Figure 2:
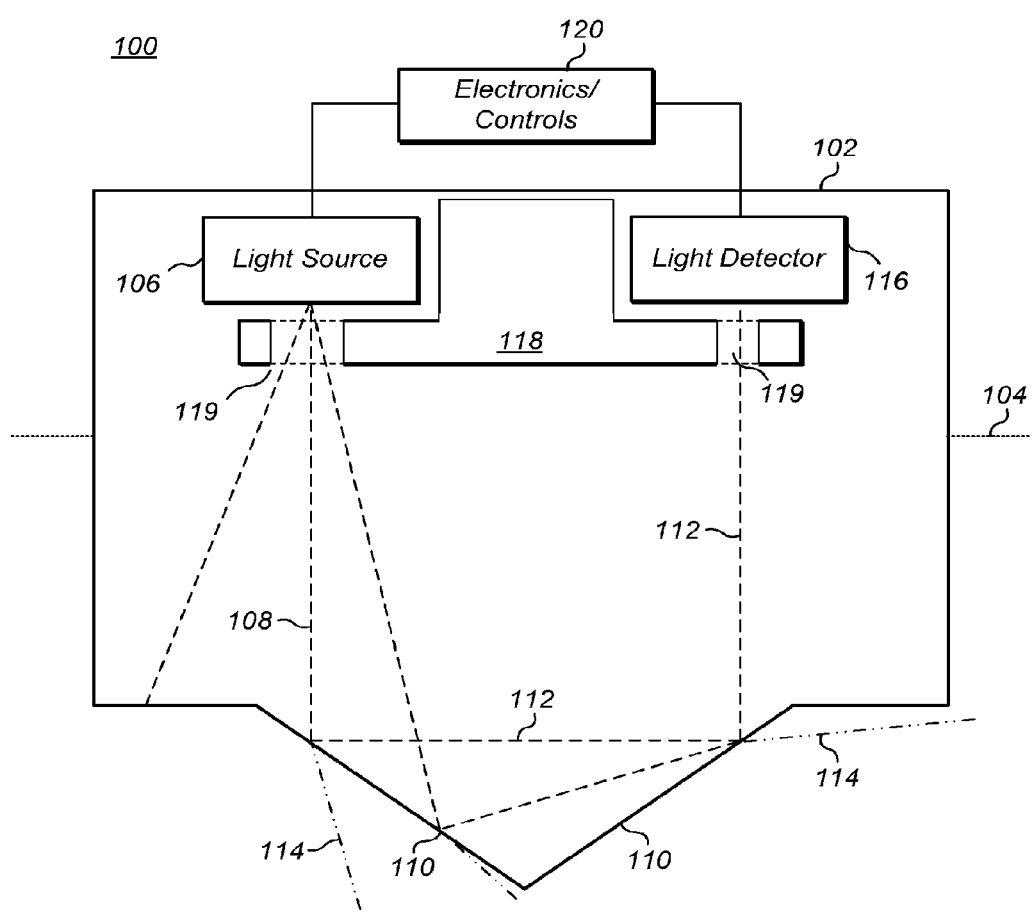
FIG. 2 is a diagram depicting a sensor for detecting fluid leakage.
Figure 6:
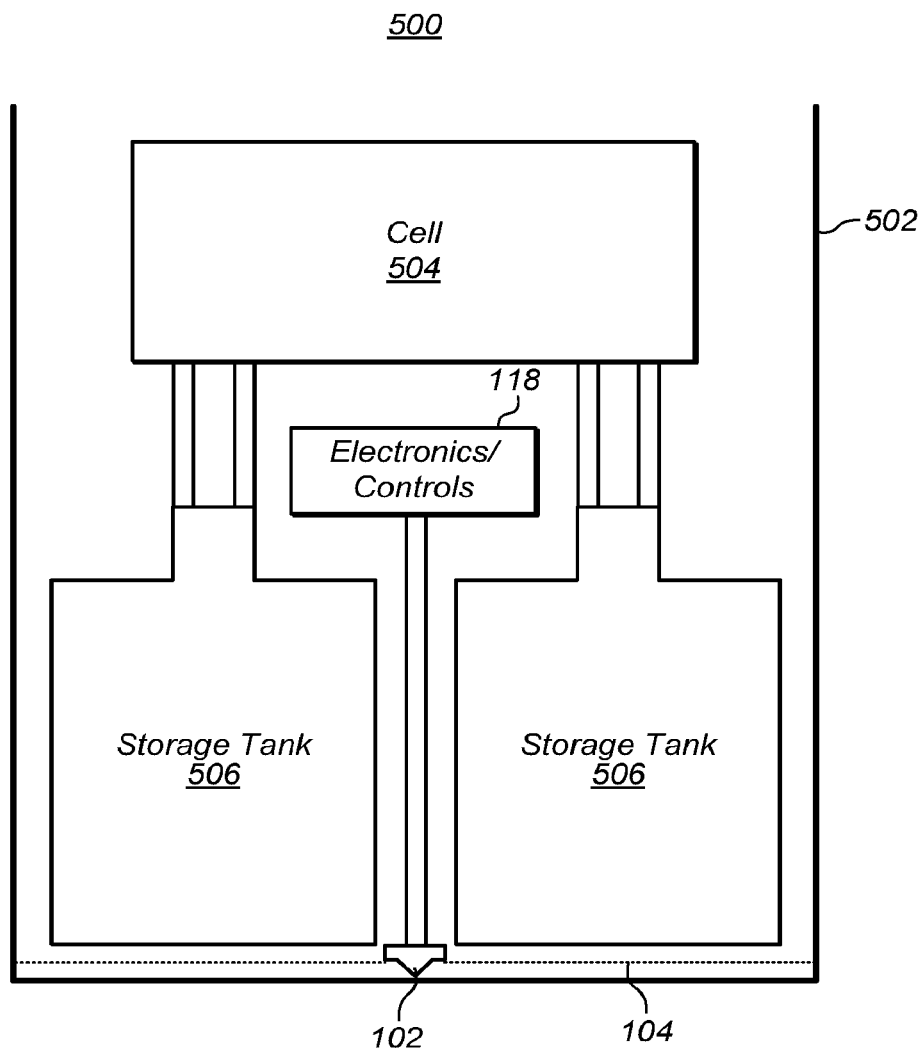
FIG. 6 is a diagram depicting a sensor for detecting fluid leakage used in a flow battery system.

FIG. 2 depicts a sensor 100 for detecting fluid leakage. As shown in FIG. 2, sensor 100 includes a sensor housing 102 which is at least partially surrounded by a fluid 104. In an embodiment, sensor housing 102 may be made of any suitable material which is resistant to corrosion (e.g., polyethylene glass or an acrylic material). In an embodiment, sensor 100 may be positioned in a flow battery system having flow battery cells and electrolyte tanks (such as the flow battery system depicted in FIG. 1). When positioned in a flow battery system, sensor 100 may be positioned at a location in a cavity of the flow battery system that is external to the electrolyte tanks In particular, sensor 100 may be placed in the flow battery system in a cavity which is at a position which is below the electrolyte tanks so as to detect any leakage of the electrolyte solution, as shown in FIG. 6. In some embodiments, multiple sensors 100 may be placed at different locations within the flow battery system, internal and/or external to the electrolyte tanks Sensor 100 further includes a light source 106 which emits light 108. Light source 106 may be, for example, a light emitting diode (LED) or a laser. Light 108 is incident on bottom surfaces 110 of sensor housing 102, wherein the light 108 is at least partially reflected 112, and partially transmitted 114 into fluid 104. In an embodiment, bottom surfaces 102 of sensor housing 102 may be surfaces of a refractor lens. As shown in FIG. 2, partially transmitted light 114 is refracted by a predetermined angle as it enters fluid 104, as will be discussed in detail below. Sensor 100 further includes light detector 116, which may detect partially reflected and refracted light 112. Light detector 116, for example, may be a photodiode. As further discussed in detail below, partially reflected and refracted light 112 has a power or intensity which depends on the refraction of emitted light 108 by fluid 104, which is indicative of the type of fluid 104 surrounding sensor housing 102. Light detector 116 measures this power, from which the type of fluid 104 surrounding sensor housing 104 may be determined. In an embodiment, light detector 116 converts the power or intensity of refracted light 112, and converts the power or intensity into a frequency, the frequency being used to determine the type of fluid 104 surrounding housing 102.

Figure 7A:
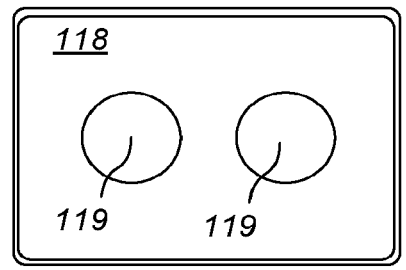
FIGS. 7A, 7B, and 7C illustrate top, cross-section, and bottom views of a shielding member illustrated in FIG. 6.
Figure 7B:
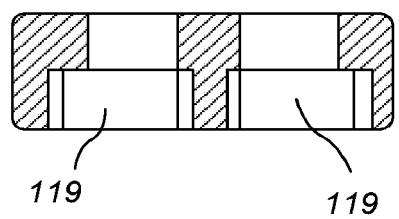
Figure 7C:
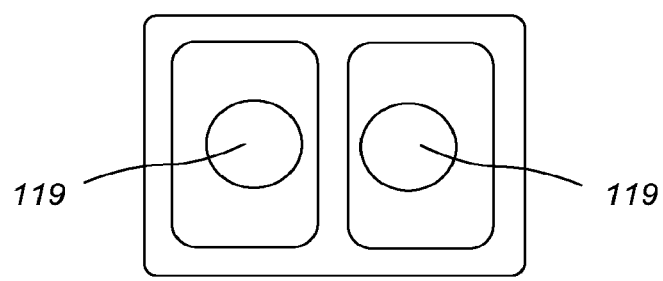

As further shown in FIG. 2, light detector 116 is partially shielded from light source 106 by shielding member 118. Shielding member 118 may prevent stray photons from emitted light 108 from being detected by light detector 116. Shielding member 118, in one embodiment, includes apertures 119, positioned in optical alignment with light source 106 and light detector 116. Top, cross-section and bottom views of shielding member 118 are depicted in FIGS. 7A, 7B and 7C, respectively.

Light source 106 and light detector 116 may also be coupled to external control electronics and controls in a control box 120, which may provide a control signal for emitting light 108 at a predetermined power and wavelength, and may further receive a signal from light detector 116 indicative of the power, or frequency of partially reflected and refracted light 112, and perform calculations to determine the type of fluid 104 surrounding sensor housing 102. The intensity or wavelength of detected light may be manifested as a current, voltage, or frequency that is produced by the detector. Control electronics may be embodied in a processor that includes processor-accessible storage medium configured to store instructions to be executed by a processor. Generally speaking, a processor-accessible storage medium may include any storage media accessible by a processor during use to provide instructions and/or data to the processor. For example, a processor accessible storage medium may include storage media such as magnetic or optical media, e.g., disk (fixed or removable), tape, CD-ROM, or DVD-ROM, CD-R, CD-RW, DVD-R, DVD-RW, or Blu-Ray. Storage media may further include volatile or non-volatile memory media such as RAM (e.g. synchronous dynamic RAM (SDRAM), double data rate (DDR, DDR2, DDR3, etc.) SDRAM, low-power DDR (LP-DDR2, etc.) SDRAM, Rambus DRAM (RDRAM), static RAM (SRAM), etc.), ROM, Flash memory, non-volatile memory (e.g. Flash memory) accessible via a peripheral interface such as the Universal Serial Bus (USB) interface, etc. Storage media may include storage media accessible via a communication medium such as a network and/or a wireless link.

Figure 3:
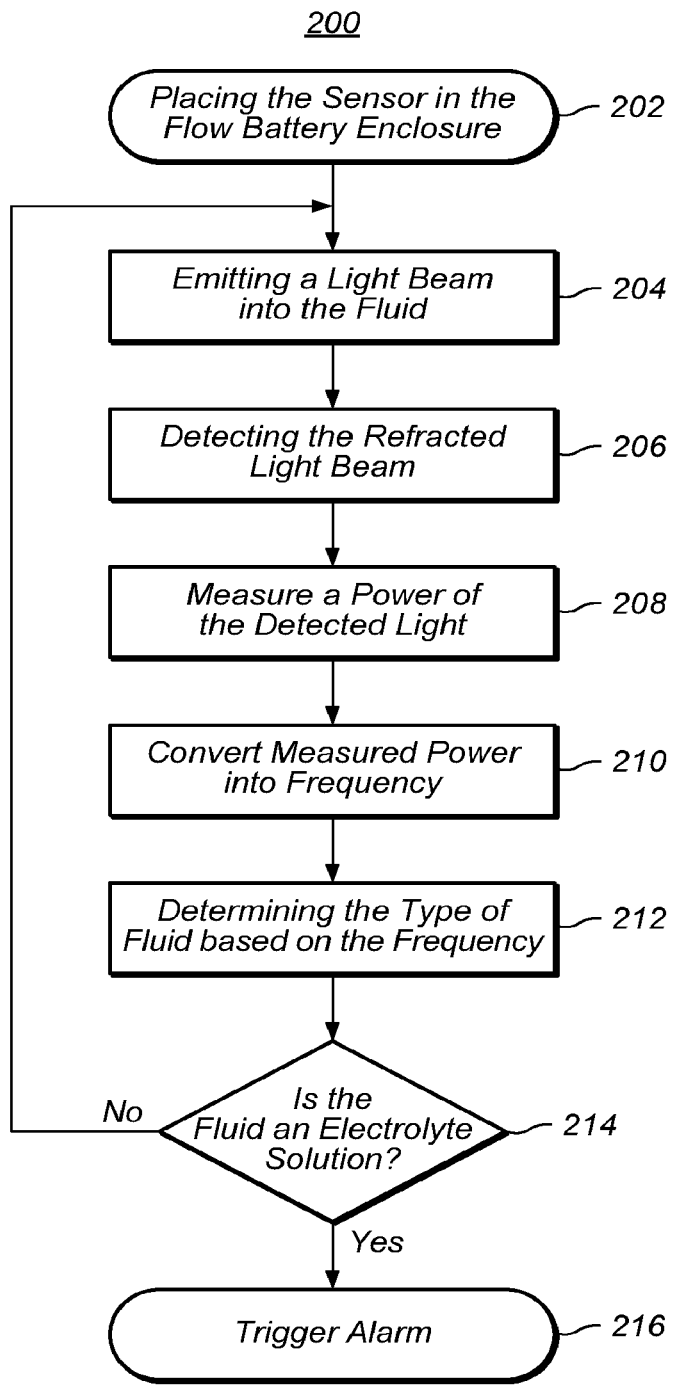
FIG. 3 is a flowchart depicting a method of detecting fluid leakage.

FIG. 3 is a flowchart illustrating a method 200 of detecting fluid leakage and will be discussed in conjunction with FIG. 2 to illustrate the operation of sensor 100 shown in FIG. 2. Sensor 100 is first placed in a desired location (202). In an embodiment, sensor 100 may be used in a flow battery system, and thus may be placed in a flow battery system enclosure. Light source 106 emits light 108 (204), which is at least partially reflected by bottom surfaces 110, and at least partially refracted by any fluid 104 disposed in the illuminated portion of the enclosure. Light detector 116 detects partially reflected light 112 (206), and measures a power of partially reflected light 112 (208). The measured power may then be converted into a corresponding frequency (210). From the frequency, the type of fluid 104 surrounding sensor housing 102 (212) may be determined. In embodiments where sensor 100 is used in a flow battery system, light detector 116 or external electronics may determine if fluid 104 is an electrolyte solution (214), thereby indicating a leak of the electrolyte solution. If fluid 104 is determined to be an electrolyte solution, light detector 116 or external electronics may trigger an alarm (216), so that a user or operator may be informed of the leak and take measures to contain or fix the leak. If fluid 104 is determined to not be an electrolyte solution, sensor 102 will emit light 108 to continue to monitor for leaks. In alternate embodiments, an indication of a leak condition may also be displayed to indicate that a leak is present, regardless of whether the leak is an electrolyte or other fluid. In some embodiments, light 108 may be emitted periodically or continuously. In addition, light 108 may be emitted on command from a user or operator.

Figure 4:
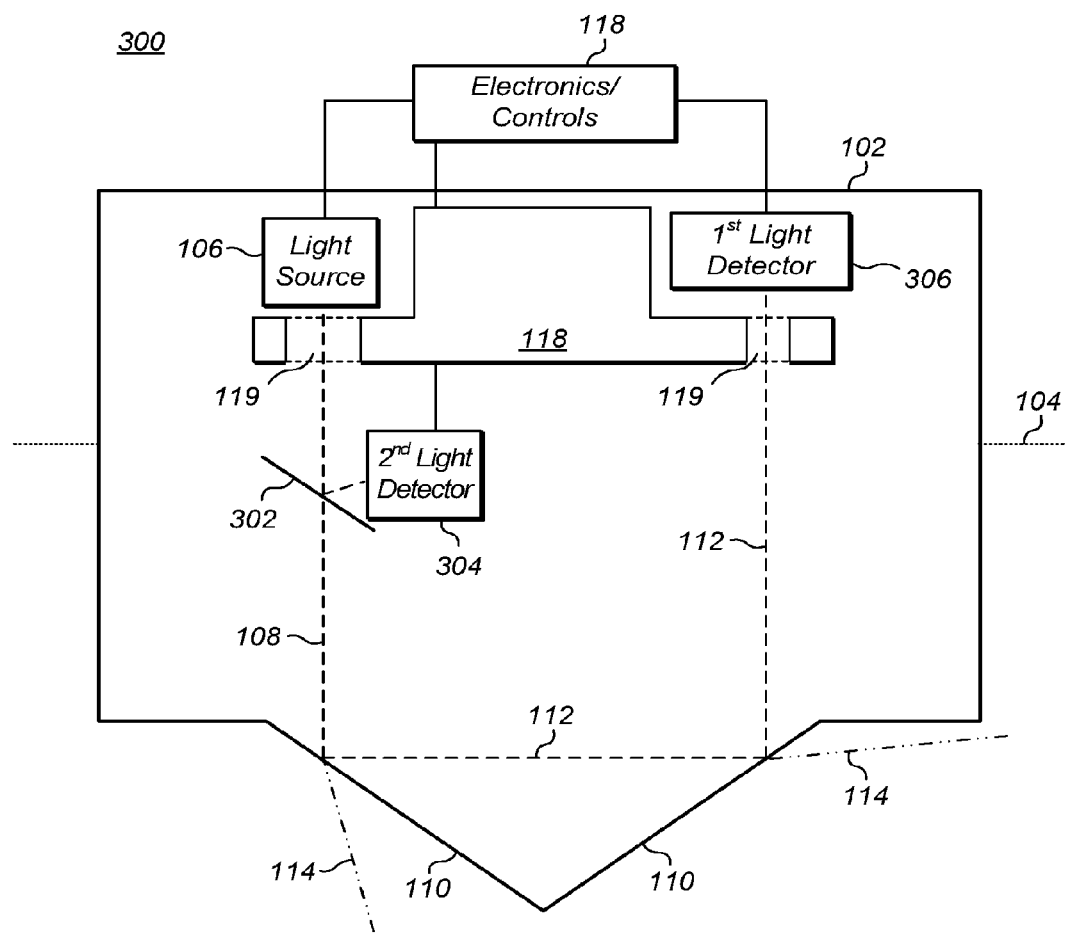
FIG. 4 is a diagram depicting a sensor for detecting fluid leakage.

FIG. 4 is a diagram illustrating a sensor 300 for detecting fluid leakage according to some embodiments. Sensor 300 is nearly identical to sensor 100 shown in FIG. 2, and operates in a nearly similar manner, and therefore the structure and operation of sensor 300 that is identical to sensor 100 is not be repeated herein. As shown in FIG. 4, sensor 300 includes a beam splitter 302 which is interposed between light source 106 and bottom surfaces 110. Beam splitter 302 diverts a portion of light 108 to a second light detector 304, which may be optically coupled to first light detector 306 or to external electronics. Consistent with at least this embodiment, second light detector 304 receives light 108 in its unattenuated state, having its initial intensity and wavelength. Light 108 detected by second light detector 304 may be used to provide an accurate reading of the initial power, wavelength, frequency, etc. of light 108, which may then be provided to external electronics in control box 120 to establish a baseline for use in comparing with partially reflected and refracted light 112 received at first light detector 306. In some embodiments, second light detector 304 may be coupled with first light detector 306 to provide a differential measurement of the power of partially reflected and refracted light 112 for determining the type of fluid 104 surrounding sensor housing 102.

As discussed above, fluid 104, may be any type of fluid, and embodiments disclosed herein may distinguish between the types of fluids. For example, fluid 104 may be air, which may be indicative that areas of the flow battery system external to the electrolyte tanks are dry and that no leak is present. Fluid 104 may also be an electrolyte solution, indicating that there is a leak. However, fluid 104 may be a different type of fluid, in particular, water. The presence of water in a flow battery system may be attributed to condensation, rain, or groundwater seepage, but does not indicate that the electrolyte tanks are leaking Accordingly, embodiments disclosed herein not only detect the presence of a fluid, but also may distinguish between different fluids such that a leak is detected only when the electrolyte solution has begun collecting in the areas of the flow battery system external to the electrolyte tanks Embodiments disclosed herein distinguish between different types of fluids using the known refractive index n of fluids.

Isotropic media such as water, air, and electrolyte solution, have different refractive indices, which are determined by the decrease or increase in velocity of light as it enters the medium. This refractive index, n, is determined by $n=c/V$ where c is the speed of light in a vacuum, and V is the phase velocity of the light wave in the medium. The refractive indices n of many common materials are known. For example, the refractive index n of air is 1, the refractive index n of water is 1.333, the refractive index n of glass is 1.5, and the refractive index n of an electrolyte solution such as used in a flow battery system is about 1.35-1.55, depending on the concentration of the electrolyte in the solution. When light is incident at a boundary between two different dielectric media, the light is at least partially reflected and partially refracted. The Law of Reflection states that the angle of incidence at this boundary is equal to the angle of reflection from the boundary. The refraction of the light is dependent on the increase or decrease of velocity of the light in that medium. The refraction may produce a change in an angle of the light such that $n_i \sin \theta_i = n_t \sin \theta_t$, $n_i$ being the refractive index of the first medium, $\theta_i$ being the angle of incidence, $n_t$, being the refractive index of the second medium, and $\theta_t$, being the angle of the light transmitted in the second medium. This is known as Snell's Law.

Figure 5:
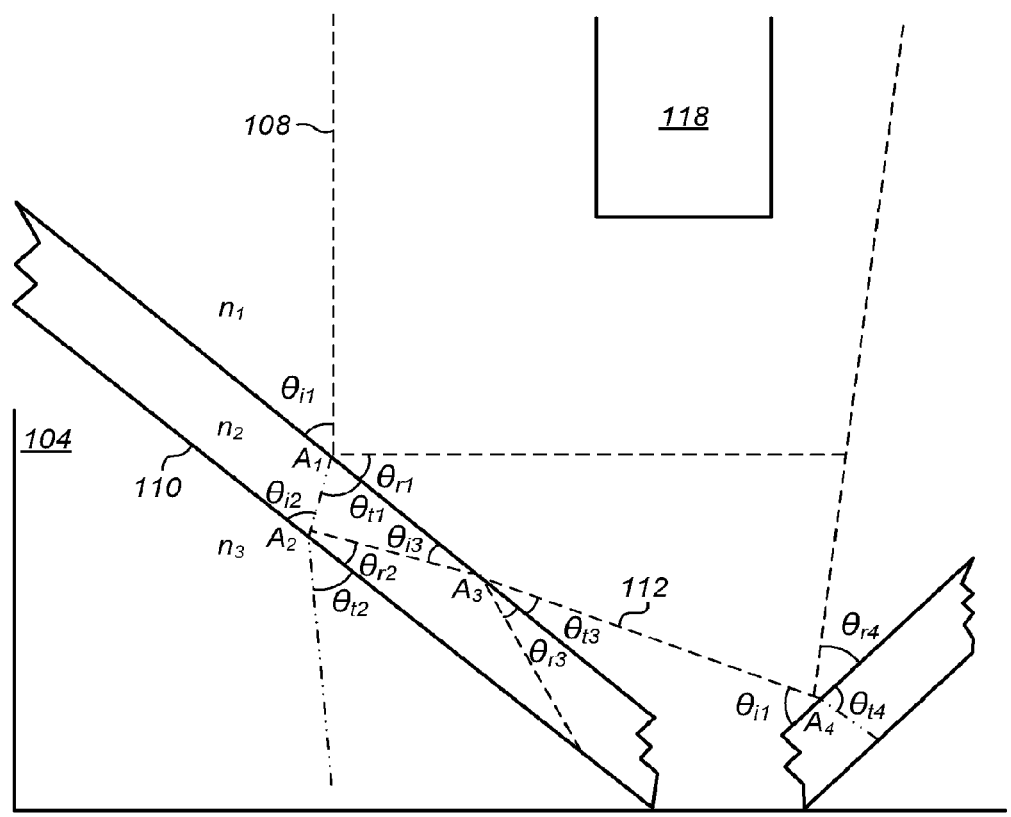
FIG. 5 is a diagram depicting the refraction of a light within a sensor.

FIG. 5 is a diagram illustrating the refraction of a light within a sensor. As shown in FIG. 5, light 108 is incident on bottom surface 110 at a first area $A_1$, at an angle of incidence $\theta_{i1}$, reflected from bottom surface 110 at an angle of reflectance $\theta_{r1}$ which is equal to the angle of incidence, and transmitted into the material of bottom surface 110 at an angle of transmission $\theta_{t1}$. In embodiments such as those shown in FIG. 5, bottom surface 110 has a non-negligible thickness such that refraction occurs as light 108 is incident on bottom surface 110. However, in some embodiments, bottom surface 110 has a negligible thickness, which does not cause substantial diffraction, such that diffraction only occurs as if light 108 were incident on fluid 104. In some embodiments, light 108 may be directed into bottom surface 110 by a waveguide or fiber optics made of the same material as bottom surface, such that no refraction occurs when light 108 is incident on bottom surface 110.

Returning to FIG. 5, the light transmitted into bottom surface 110 is incident on fluid at a second area $A_2$, at an angle of incidence $\theta_{i2}$, which is equal to $\theta_{t1}$, reflected off bottom surface 110 at an angle of reflectance $\theta_{r2}$ which is also equal to the angle of incidence, and transmitted into fluid 104 at an angle of transmission $\theta_{t2}$. The light reflected off fluid 104 is again incident on bottom surface 110 at a third area $A_3$, at an angle of incidence $\theta_{i3}$, which is equal to $\theta_{r1}$, reflected off bottom surface 110 at an angle of reflectance $\theta_{r3}$ which is also equal to the angle of incidence, and transmitted into sensor housing 102 at an angle of transmission $\theta_{t3}$. The light transmitted into the interior of sensor housing 102 is then incident at a fourth area $A_4$ on bottom surface 110, at an angle of incidence $\theta_{i4}$, reflected off bottom surface 110 at an angle of reflectance $\theta_{r4}$ which is also equal to the angle of incidence, and transmitted into bottom surface 110 at an angle of transmission $\theta_{t4}$. As shown in FIG. 5, the reflected light 112 having an angle of reflectance of $\theta_{r4}$ is transmitted to light detector 116. Using Snell's Law and the Law of Reflection, above, and knowing the initial angle of incidence, and the refractive indices $n_1$, $n_2$, and $n_3$, respectively, for sensor housing 102, bottom surface 110, and fluid 104, all of the angles of incidence, transmittance, and reflectance can be determined. Similarly, knowing each of the angles of incidence, transmittance, and reflectance, as well as the refractive indices $n_1$ and $n_2$, respectively, for sensor housing 102 and bottom surface 110, the refractive index $n_3$ for fluid 104 can be determined.

In some embodiments, sensor 100 determines refractive index $n_3$ of fluid 104, and thereby determines the type of fluid 104, by measuring a power of the at least partially reflected and partially refracted light 112 received by light detector 116. The power of a light incident at an area A, such as areas $A_1$-$A_4$, is given by the equation:

$$I_i A \cos \theta_i = I_r A \cos \theta_r + I_t A \cos \theta_t,$$

where A is the surface area of incidence, I is the radiant flux density of the incident, reflected, and transmitted light, and $\theta$ is the angle of incidence, reflectance, and transmittance. From this equation, the power at each of the four areas of incidence $A_1$-$A_4$ can be determined. As can be determined using the above equation in conjunction with FIG. 5, the total power of partially refracted light 112 received by light detector 116 is less than a power of initial light 104 due to refraction. The power or intensity of the partially refracted light 112 detected by light detector 116 may then be converted into a corresponding frequency. As shown in FIG. 3, the frequency may then be compared with predetermined frequencies to determine the type of fluid 104. As shown in FIG. 3, if fluid 104 is determined to be an electrolyte solution, a leak is detected, and an alarm may be triggered. However, if fluid is determined to be, for example, water or air, a leak is not present, and sensor 100 continues to monitor for leakage. Alternatively, the composition of fluid in contact with at least a portion of the bottom surfaces of the leak detector may be determined based on a current output and/or voltage output of the detector in response to the incident light.

In some embodiments, the refractive index $n_3$ may be measured in order to determine the type of fluid 104. Using Snell's Law and the Law of Reflectance above, as well as trigonometric identities, an equation for the power of the light reflected off bottom surface 110 at angle of reflectance $\theta_{r4}$ can be determined which is in terms of the initial power of light 108, and refractive indices $n_1$, $n_2$, and $n_3$. By knowing the initial power of light 108, and the value of the refractive indices $n_1$ and $n_2$ of sensor housing 102 and bottom surface 110, a value for the refractive index $n_3$ of fluid 104 may be determined. The determined refractive index $n_3$ of fluid is then compared with known refractive indices to determine the type of fluid 104. As shown in FIG. 3, if fluid 104 is determined to be an electrolyte solution, a leak is detected, and an alarm may be triggered. However, if fluid is determined to be, for example, water or air, a leak is not present, and sensor 100 continues to monitor for leakage.

In some embodiments, sensor 100 is operated when fluid 104 is air and the frequency of the signal output from light detector 116 is noted. In this fashion, sensor 100 may be calibrated against air. The frequency of light will decrease as the index of fluid 104 increases and may become close to zero when the index of fluid 104 matches the index of bottom surface 110. The concentration of electrolyte in fluid 104 can be determined by the decrease of the frequency of the signal from light detector 116 in comparison with the frequency of the signal from light detector 116 when fluid 104 is air. Sensor 100 may be calibrated against other fluids such as water or some other fluid that may potentially be present.

FIG. 6 is a diagram illustrating a sensor for detecting leakage 102 used in a flow battery system 500, according to some embodiments. As shown in FIG. 6, flow battery system 500 includes a flow battery cabinet 502, which houses a flow battery cell 504 that is coupled to electrolyte storage tanks 506. Although FIG. 6 illustrates two electrolyte storage tanks 506, consistent with some embodiments, flow battery cabinet may house more than two electrolyte storage tanks 506. As shown in FIG. 6, sensor housing 102 is positioned at a bottom portion of flow battery cabinet 502 so as to detect any fluid 104 which may be collecting in the bottom portion of flow battery cabinet 502. In some embodiments, sensor housing 102 corresponds to sensor 100. In some embodiments, sensor housing 102 corresponds to sensor 300. Sensor housing 102 is electrically coupled to external electronics and controls 118, which transmits and receives signals to and from sensor housing 102 for detecting the presence of fluid 104, and determining the type of fluid 104. As shown in FIG. 3, if fluid 104 is determined to be an electrolyte solution, a leak from electrolyte storage tanks 506 or flow battery cell 504 is detected, and external electronics/controls 118 may trigger an alarm. If fluid is determined to be, for example, water or air, a leak is not present, and the sensor continues to monitor for leakage of electrolyte.

Accordingly, some embodiments as disclosed herein may provide a leakage sensor which is not only able to detect the presence of a fluid, determine the type of fluid, and determine whether the fluid is a leaking fluid that poses a potential problem.

In this patent, certain U.S. patents, U.S. patent applications, and other materials (e.g., articles) have been incorporated by reference. The text of such U.S. patents, U.S. patent applications, and other materials is, however, only incorporated by reference to the extent that no conflict exists between such text and the other statements and drawings set forth herein. In the event of such conflict, then any such conflicting text in such incorporated by reference U.S. patents, U.S. patent applications, and other materials is specifically not incorporated by reference in this patent.

Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as examples of embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A leak detector for detecting leakage of an electrolyte solution comprising:
   a device housing, the device housing comprising bottom surfaces;
   at least one light source in the device housing, the at least one light source emitting light that at least partially reflects from the bottom surfaces of the device housing, and is at least partially refracted by the bottom surfaces and fluid in contact with at least a portion of the bottom surface that the light is incident upon; and
   at least one light detector in the device housing, the light detector receiving the partially reflected light to obtain a measured light intensity; and
   control electronics coupled to the leak detector;
   wherein the control electronics determine type of fluid in contact with at least a portion of the bottom surfaces of the leak detector based on the difference between the measured light intensity and the intensity of light produced by the light source so that leakage of the electrolyte solution is detected.

2. The leak detector of claim 1, wherein the leak detector produces continuous output of the fluid surrounding the leak detector.

* * * * *